United States Patent [19]
Pages et al.

[11] Patent Number: 5,954,971
[45] Date of Patent: Sep. 21, 1999

[54] PUMPED-FILTER BLOOD-PROCESSING APPARATUS AND METHODS

[75] Inventors: Etienne Pages, Arlington, Mass.; Alain Dransart, Gland, Switzerland; Yair Egozy, Lexington, Mass.; Yves Baratelli, Lully, Switzerland

[73] Assignee: Haemonetics Corporation, Braintree, Mass.

[21] Appl. No.: 08/779,912

[22] Filed: Jan. 7, 1997

[51] Int. Cl.$^6$ .............................. B01D 37/00; B01D 36/00
[52] U.S. Cl. .............................. 210/739; 210/85; 210/87; 210/90; 210/97; 210/103; 210/109; 210/143; 210/252; 210/257.1; 210/258
[58] Field of Search ...................................... 210/645, 739, 210/741, 767, 782, 85, 87, 90, 97, 103, 109, 143, 252, 258, 257.1; 604/4, 5, 6, 65, 67

[56] References Cited

U.S. PATENT DOCUMENTS

| | | | |
|---|---|---|---|
| 4,565,626 | 1/1986 | Azuma et al. | 210/138 |
| 4,648,866 | 3/1987 | Malbrancq et al. | 604/5 |
| 4,678,566 | 7/1987 | Watannabe et al. | 210/143 |
| 4,897,189 | 1/1990 | Greenwood et al. | 210/195.2 |
| 4,929,363 | 5/1990 | Barzuza | 210/741 |
| 5,069,792 | 12/1991 | Prince et al. | 210/651 |
| 5,100,564 | 3/1992 | Pall et al. | 210/782 |
| 5,112,298 | 5/1992 | Prince et al. | 604/6 |
| 5,194,145 | 3/1993 | Schoendorfer | 210/90 |
| 5,211,850 | 5/1993 | Shettigar et al. | 210/645 |
| 5,269,924 | 12/1993 | Rochat | 210/445 |
| 5,344,568 | 9/1994 | Kitaevich et al. | 210/645 |
| 5,387,187 | 2/1995 | Fell et al. | 604/6 |
| 5,403,272 | 4/1995 | Deniega et al. | 604/4 |
| 5,427,695 | 6/1995 | Brown | 210/782 |
| 5,431,811 | 7/1995 | Tusini et al. | 210/90 |
| 5,460,715 | 10/1995 | Kawamura et al. | 210/97 |
| 5,536,238 | 7/1996 | Bischof | 604/6 |
| 5,643,794 | 7/1997 | Liu et al. | 604/5 |
| 5,690,815 | 11/1997 | Krasnoff et al. | 210/85 |
| 5,865,785 | 2/1999 | Bischof | 604/5 |

FOREIGN PATENT DOCUMENTS

| | | |
|---|---|---|
| 0 156 496A1 | 10/1985 | European Pat. Off. . |
| 0 240 101 A2 | 10/1987 | European Pat. Off. . |
| 0 349 188A1 | 1/1990 | European Pat. Off. . |
| WO93/01858 | 2/1993 | WIPO . |

*Primary Examiner*—John Kim
*Attorney, Agent, or Firm*—Cesari and McKenna, LLP

[57] ABSTRACT

Automated filtration of whole blood or blood components is accomplished in a manner that ensures consistent flow or pressure characteristics through the filter. A feedback circuit monitors pressure in the vicinity of the filter inlet and controls operation of a fluid pump that sends one or more unfiltered blood components into the filter. Using this arrangement, a variety of parameters relating to filtration efficacy can be precisely controlled, including flow rate, flow pressure, and average pressure over a predetermined volume. The system may provide an alarm or automatic cut-off in the event a maximum value of one of the parameters is reached or exceeded. The system is also capable of serially filtering multiple blood products through the single filter and accommodating different flow or pressure characteristics associated with each such product.

31 Claims, 4 Drawing Sheets

PUMPED-FILTER BLOOD-PROCESSING APPARATUS AND METHODS

FIELD OF THE INVENTION

This invention relates to medical equipment, and in particular to apparatus for separating whole blood into components for collection.

BACKGROUND OF THE INVENTION

Whole human blood includes predominantly three types of specialized cells: red blood cells, white blood cells, and platelets. These cells are suspended in a complex aqueous solution of proteins and other chemicals called plasma. Although in the past blood transfusions have used whole blood, the current trend is to transfuse only those blood components required by a particular patient. This approach preserves the available blood supply and in many cases is better for the patient, since the patient is not exposed to unneeded blood components. Storage lifetimes can also be increased by packaging the individual blood products separately.

The blood components needed for transfusion may be taken from a donor by a process called apheresis in which the desired one, or more, specific components of the whole blood are separated and harvested by a blood-processing machine. The remaining components are returned to the donor. (As used herein, the term "donor" connotes anyone from whom blood is drawn for collection or processing, and can include volunteer donors, paid donors or medical patients to whom collected blood components are returned.)

Traditionally, blood components have been filtered by gravity to remove potentially deleterious contaminants or endogenous constituents, such as white blood cells or "leukocytes." Although leukocytes provide a host with protection against bacterial and viral infection, their introduction into a transfusion recipient can cause highly adverse reactions not elicited by other blood products. For example, transfused leukocytes can provoke severe immunogenic rejection reactions, viral diseases and organ damage. Accordingly, it is desirable to filter harvested blood fractions such as plasma, platelets or red blood cells to remove leukocytes.

In a typical arrangement, the blood component resides within a container in fluid communication with the inlet to a leukocyte filter and suspended thereabove; exiting filtrate is collected in a container disposed below the filter and in fluid communication with its outlet. The vertical distance between the blood component and the receiving bag is generally 20 to 60 inches.

The flow rate at which filtration occurs may vary considerably as the process proceeds. This is due primarily to gradual plugging of the filter, which increases the resistance to flow. Thus, in many cases, the flow at the onset of filtration is twice that observed at the conclusion. The filtration rate can also vary as a result of differences in blood properties among donors.

This variation can have a significant impact on filtrate quality, since filtration efficiency typically depends on contact time between the unfiltered blood component and the filter material. As the flow rate increases, for example, contact time decreases, and the concentration of unremoved leukocytes in the filtrate may therefore rise. At the same time, it is desirable to avoid needlessly low flow rates that increase the duration of the process beyond what is necessary to achieve satisfactory filtrate purity.

Generally, leukocyte filters have an appreciable internal volume, and gravity filtration is poorly suited to removing the final quantity of blood product remaining in the filter. An auxiliary fluid can, of course, be used to purge the filter and cause exit and collection of this remaining quantity, but the equipment and procedures necessary to implement this are both cumbersome and labor intensive.

DESCRIPTION OF THE INVENTION

SUMMARY OF THE INVENTION

The present invention automates the process of filtration in a manner that ensures consistent flow or pressure characteristics through the filter. In a first aspect, the invention comprises a feedback circuit that monitors pressure in the vicinity of the filter inlet. The feedback circuit controls the operation of a fluid pump that sends one or more unfiltered blood components into the filter. Using this arrangement, a variety of parameters relating to filtration efficacy can be precisely controlled. One such parameter is flow rate; if the displaced volume is not directly determined by the pump rate, pressure can be used as a surrogate to monitor flow rate and control the pump accordingly.

In the preferred embodiment, however, the pump is a volumetric pump, so that constant flow results directly from a constant pumping rate. For such systems, the controlled parameter is typically filter pressure. It is important, in enforcing a constant flow rate, to avoid imposing excessive pressures on the filter. Moreover, some filters are more sensitive to pressure than flow rate, and may require a constant pressure for optimal performance. In the former case, the feedback circuit may include an alarm that alerts an operator when enforcement of the constant flow rate results in excessive pressures at the filter inlet (corresponding to the trans-filter pressure since, at a constant flow rate, the outlet pressure is substantially constant). In addition, the feedback circuit can be configured to terminate flow at the pressure limit. In the latter case, the feedback circuit operates the pump so that the pressure at the filter inlet remains constant. The pressure alarm limit can be the maximum pressure safely tolerated by the filter, but more commonly will be a value which, when exceeded, compromises the quality of the filtrate.

Some filters tolerate intermittent pressure spikes, so long as the average pressure over a given volume of flow does not exceed some maximum. In this case, the feedback circuit integrates pressure readings over a predetermined flow volume and causes actuation of the alarm and/or termination of flow if the average pressure exceeds the maximum limit.

In a second aspect, the invention facilitates convenient purging of the interior filter volume following completion of the filtration process. The system includes a selectively connected source of auxiliary fluid, such as saline or a preservation solution, which the pump sends through the filter after exhaustion of the unfiltered blood product. Sufficient auxiliary fluid passes through the filter to clear most of the remaining blood product and, if desired, also to rinse the filter.

In a third aspect, the invention facilitates filtration of multiple blood products through the same filter, with the different filtrates each collected in a separate container. The feedback circuit accommodates the different flow or pressure characteristics that may be desirable for filtration of the various blood products.

In a fourth aspect, the invention provides a complete apheresis system for the withdrawal and separation of blood, preceded by filtration of whole blood and/or followed by filtration and collection of the separated fractions. The system includes a phlebotomy need for withdrawing blood from a donor, a centrifuge for separating the blood into components, a filter, pumps, a controller and pressure sensor operating, inter alia, as the feedback circuit, and the various containers, plumbing, mechanical and electronic components necessary to effectuate an apheresis procedure according to well-established protocols.

The invention accordingly includes apparatus configured to operate in accordance with the foregoing principles, as well as methods embodying them.

BRIEF DESCRIPTION OF THE DRAWINGS

The foregoing discussion will be understood more readily from the following detailed description of the invention, when taken in conjunction with the accompanying drawings, in which.

Figure 1:
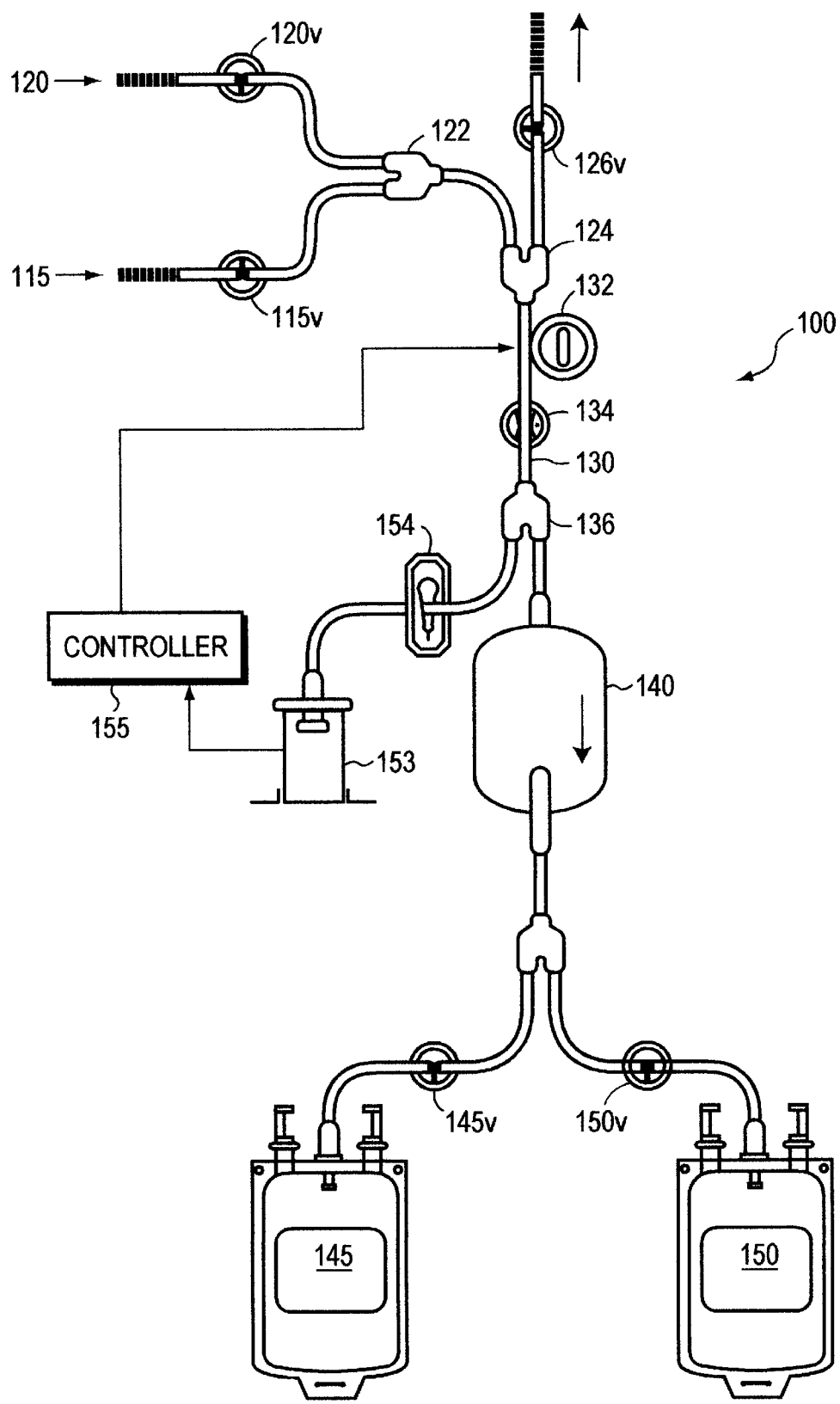
FIG. 1 is a simplified schematic representation of an apheresis apparatus embodying the key features of the present invention.

Throughout the different figures, reference numerals differing in their first digit refer to the same components.

DETAILED DESCRIPTION OF THE PREFERRED EMBODIMENTS

Refer first to FIG. 1, which depicts the basic elements of an apparatus, indicated generally at 100, in accordance with the present invention. The apparatus 100 includes first and second inlets 115, 120 that admit fluid into a pair of blood-compatible tubing branches by way of a pair of valves 115v, 120v, respectively. The tubing branches join at a Y-connector 122, the outlet of which is fluidly coupled to one inlet of a second Y-connector 124. The other inlet of Y-connector 124 is fluidly coupled, via a check valve 126v, to an air container (not shown) or vent.

Emerging from the outlet of Y-connector 124 is a main blood-compatible tubing line 130 that operatively engages a controllable, bidirectional peristaltic pump 132; pump 132, in turn, determines the fluid direction and flow pressure within tubing 130 and its branches. Air within tubing 130 is sensed by an air detector 134. Tubing 130 divides at a third Y-connector 136, a first outlet of which is fluidly coupled to the inlet of a filter 140. Material exiting filter 140 is conducted to either of two collection bags 145, 150 as determined by the settings of a pair of valves 145v, 150v. The function and structure of filter 140 depends on the nature of the material being filtered, and may be, for example, a leukocyte filter (e.g., the BPF4 or LRF6 filter marketed by Pall Biomedical Corp., East Hills, N.Y., or the R200 filter available from Asahi Sepacell, Tokyo, Japan); a viral filter for inactivation or reduction of viruses (e.g., the STERIPATH filter made by Hemasure Inc., Marlborough, Mass.); a bacterial filter; or a platelet-removal filter. These components are conventional and readily available.

The other outlet of Y-connector 136 leads to a pressure sensor 153, which determines the fluid pressure within the line 130 and its open branches, and produces an electronic signal indicative thereof. Sensor 153 preferably includes a hydrophobic filter to isolate the sterile interior environment of apparatus 100 from external pathogens, and may be fluidly segregated from the system during installation by means of a tubing slide clamp 154. The signal output of sensor 153 is provided to a controller 155, which determines, via suitable electrical connections and control signals, the state of pump 132.

In operation, the system is first purged of air by closing valves 115v and 120v and running pump 132 in reverse until a desired internal pressure (e.g., 75 mm Hg below atmospheric), as measured by pressure sensor 153, is reached. Air in the system is rejected through check valve 126v. Valve 115v is then opened, allowing one or more blood components (e.g., whole blood, plasma, platelet-rich plasma, etc.) then enter the system through inlet 115. Pump 132 is operated to draw material through inlet 115 and force it through filter 140 into one of the collection bags 145, 150. As this process proceeds, the pressure at the inlet to filter 140 (as measured by sensor 153) increases as filter 140 gradually plugs. In response to the increased resistance to flow, controller 155 operates pump 132 in a manner consistent with the capabilities of the invention and the selection of the operator. In particular, controller 155 may maintain a constant flow but terminate pumping if a maximum pressure is reached; maintain a constant internal pressure by varying the flow; or maintain some combination of a target flow rate and a target or maximum pressure (e.g., controller 155 may enforce a constant flow rate for a given flow volume or period of time, or within a pressure range, then enforce a constant pressure for the remainder of a cycle). Again, because pump 132 is a volumetric pump, the flow rate dV/dt follows directly from the pump rotation (pumping) rate. Sensor 153 and controller 155 form a feedback circuit that enforces a programmed pressure/flow rate regime. As a result, optimal filter performance may be ensured.

Controller 155 can also be provided with an alarm function that alerts the system operator (e.g., by means of a light, a display message or an audible signal) and/or shuts down pump 132 if the measured pressure exceeds a maximum limit. For example, blood cells can be physically damaged if flow pressure rises above a maximum tolerance level. This level is programmed into controller 155 and used as the alarm limit. Controller 155 may itself be implemented, for example, using a programmable, single-chip microcomputer which incorporates analog-to-digital converters for transforming the signals from sensor 153 into digital signals that may be processed by the microcomputer. Alternatively, the circuitry may be implemented in a custom integrated circuit or in discrete electronics. Controller 100 may also include a keypad or other input/output device for receiving data from the system operator.

Figure 3:
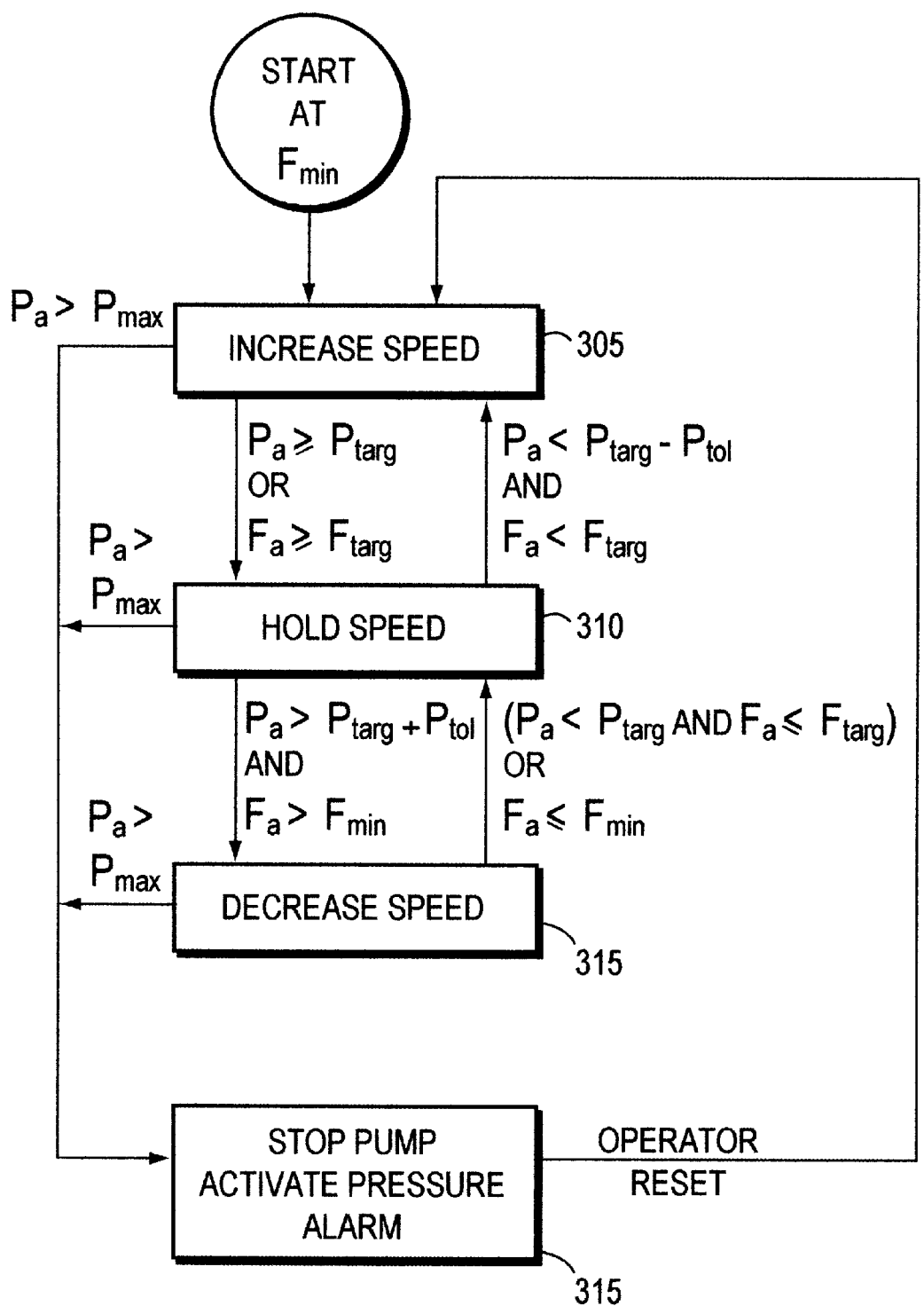
FIG. 3 is a state diagram illustrating operation of the controller of the present invention.

Representative programming logic for controller 155 is shown as a state diagram in FIG. 3. Controller 155 receives, on a frequent or continuous basis, data representing the actual pressure $P_a$ at the inlet to filter 140 (as measured by sensor 153) and the actual flow rate $F_a$ from pump 132 (which is constant if pump 132 is a volumetric pump, but which may otherwise be calculated from $P_a$). The operator provides controller 155 with values representing one or more of a maximum pressure $P_{max}$, a target pressure $P_{targ}$, a pressure tolerance $P_{tol}$ (i.e., an expected deviation arising from, for example, small pressure fluctuations associated with the pump rollers or measurement error, the $P_{tol}$ parameter functioning as a threshold to prevent inappropriately fine pump adjustments), a target flow rate $F_{targ}$ and a minimum flow rate $F_{min}$. The illustrated logic assumes provision of values for all these parameters.

Controller continuously analyzes the data it receives (which may change) and the data provided by the operator (which remains constant during a cycle) in accordance with the illustrated logic to determine the state of the system. At startup, controller 155 causes the system to enter the state 305, corresponding to increasing the speed of pump 132, until $P_a \geq P_{targ}$ or $F_a \geq F_{targ}$, at which point the system enters the state 310, where pump speed is held constant. If, however, $P_a$ exceeds $P_{max}$ at any point, the system enters the alarm state 315, where pump 132 is stopped and/or an alarm activated.

State 310 is maintained until any of three conditions is detected: (1) $P_a < P_{targ} - P_{tol}$ and $F_a < F_{targ}$, in which case controller 155 causes the system to re-enter state 305; or (2) $P_a > P_{targ} + P_{tol}$ and $F_a > F_{min}$, in which case controller 155 causes the system to enter the state 320, corresponding to decreasing the speed of pump 132; or, once again, $P_a > P_{max}$, whereupon the system enters alarm state 315. Controller 155 causes the system to leave state 315 upon detection of any of three conditions: (1) $P_a < P_{targ}$ and $F_a \leq F_{targ}$; (2) $F_a \leq F_{min}$; or (3) $P_a > P_{max}$. Conditions (1) or (2) cause the system to revert to state 310, while condition (3) results in entry of the alarm state 315.

From alarm state 315, the system can be restarted (in state 305) upon operator reset.

Figure 4:
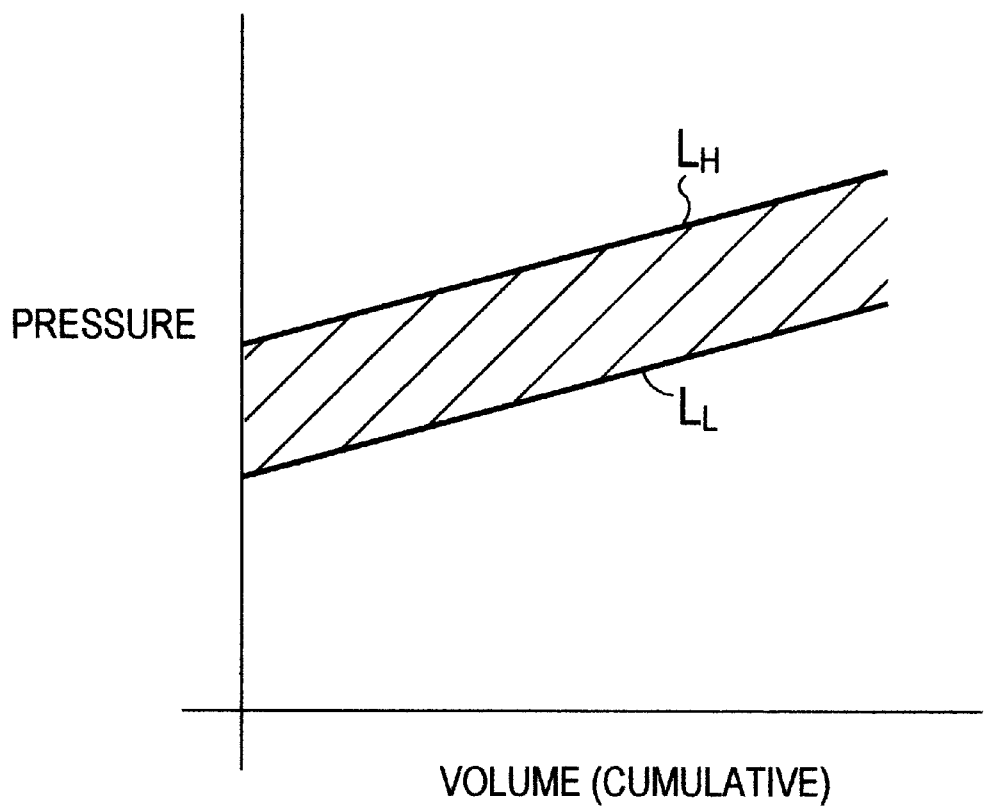
FIG. 4 graphically depicts a representative filter quality profile that may be used to govern operation of the present invention.

The alarm limit may be more complex than a single-valued pressure level. For example, as shown in FIG. 4, tolerable filter pressure can be a function of cumulative filtered volume, so that small pressure "spikes" are acceptable so long as the average pressure over a given volume remains within a certain limit $L_H$. Indeed, optimal filtration efficacy may also require a minimum pressure $L_L$, so that a quality filtrate is assured only when the pressure remains within the bounds of $L_H$ and $L_L$ during operation. Excessively high or low pressures can also indicate basic malfunction or defect; for example, insufficient flow resistance may reflect a filter bypass or leak, while excessive resistance may result from mispriming or an inoperative filter. Either condition indicates the need to check the final product for quality. Conversely, proper operation within the acceptable range provides some degree of quality assurance. If desired, a normally closed bypass loop around filter 140 can also be provided so that, if the alarm limit is reached, the path through filter 140 may be closed and unfiltered blood component(s) diverted to a collection container to avoid loss or contamination as a result of contact with a malfunctioning filter.

Inlet 120 may be used to admit various auxiliary fluids for different purposes during the course of filtration and collection. For example, saline solution may be introduced prior to entry of blood component(s) through inlet 115 in order to prime the system tubing and/or filter 140. In addition, after introduction of a blood component through inlet 115 is complete, a fluid may be fed through inlet 120 in order to displace into a collection bag material remaining in filter 140, which may have an internal volume on the order of 30 mL.

Various changes are feasible for the embodiment shown in FIG. 1. For example, pump 132 can be located downstream of filter 140 (i.e., between filter 140 and the Y-connector leading to valves 145v, 150v), drawing blood through filter 140 instead of driving it through. An air-elimination vent with a check valve (as described below) to facilitate purging of air may also be added downstream of filter 140, as may a sample bag to collect a small amount of filtrate prior to completion of a cycle.

Figure 2:
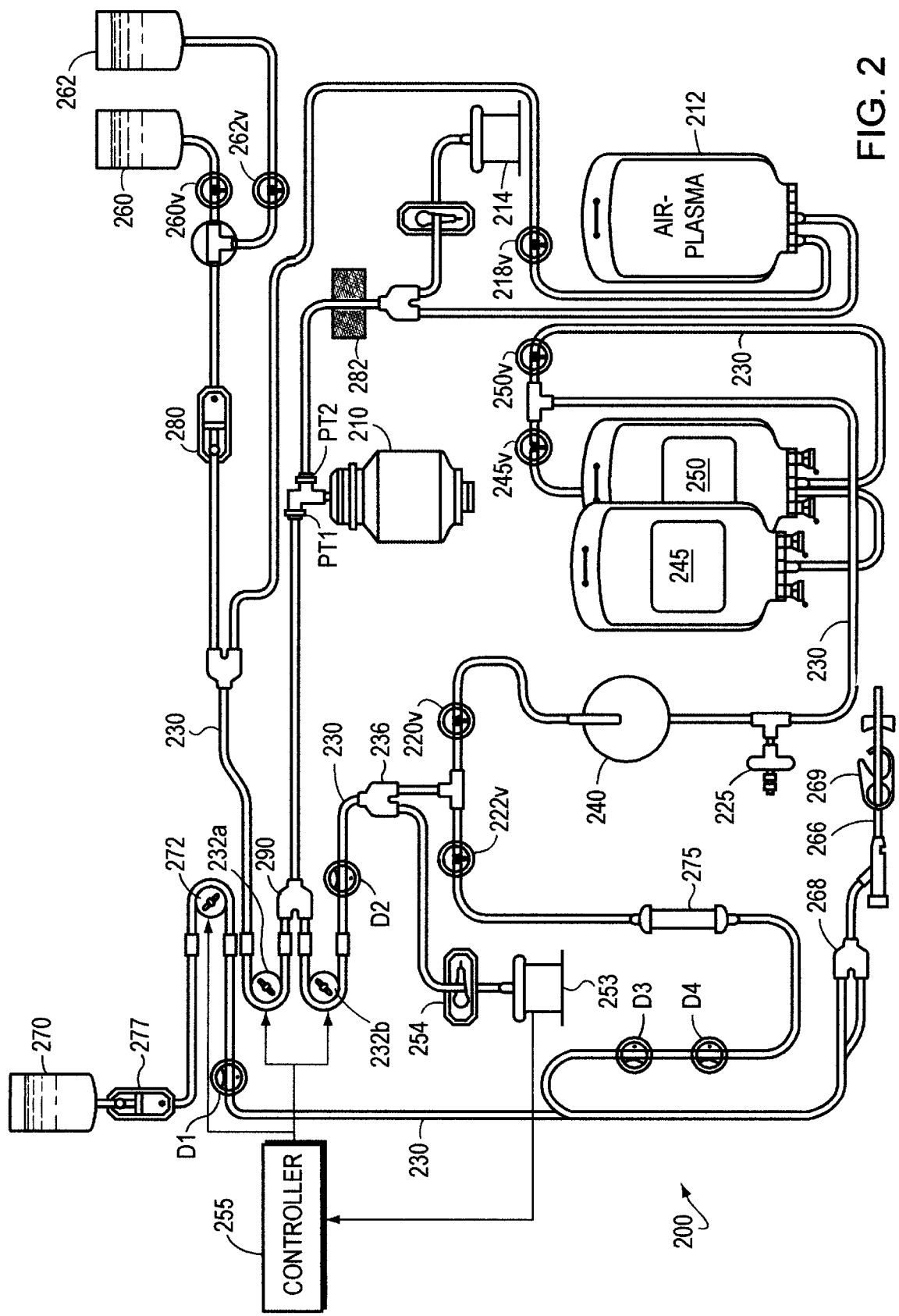
FIG. 2 is a schematic representation of a more elaborate embodiment of the present invention.

In typical usage, the source of blood component(s) will be an apheresis apparatus that collects blood from a donor and separates it into fractions such as plasma, buffy coat, platelets and red blood cells ("RBC"), or some combination thereof. FIG. 2 illustrates a more elaborate embodiment of the present invention that operates as a self-standing apheresis apparatus for collection of red blood cells. The device 200 utilizes a conventional centrifuge bowl 210 (in accordance, for example, with U.S. Pat. No. 4,983,158) having an internal fluid capacity preferably on the order of 250 ml, means (not shown) for rotating the bowl, an inlet port PT1 and an outlet port PT2. Outlet port PT2 of centrifuge bowl 210 is in fluid communication with the inlet port of a container 212 for collecting plasma and air during the course of operation; container 212 is oriented vertically, as illustrated, so that collected liquid and not air is drained from container 212 in withdrawal modes. The fluid path from outlet port PT2 also includes a pressure sensor 214 for monitoring pressure within the system. The fluid path from the outlet port of container 212 returns, via a valve 218v, to the primary peristaltic pumps 232a, 232b that implement most system functions, and thereafter, via a pair of valves 220v, 222v, to the inlet port of filter 240. The fluid path from the outlet port of filter 240 includes a hydrophobic vent 225 and leads, via valves 245v, 250v, to first and second collection bags 245, 250. These are used to store filtered red cells obtained from a donor.

Also connected to the return path from the outlet port of container 212 are a pair of containers 260 (for saline solution) and 262 (for a preservation agent), which couple to the fluid path via a pair of valves 260v, 262v. The preservation agent is an additive for extending the shelf life of RBC, suitable examples of which include SAGM, ADSOL, NUTRICELL, PAGGsM, MAP and glycerol.

Inlet port PT1 of centrifuge 210 is selectively coupled, via valves 220v, 222v and a Y-connector 268, to a phlebotomy needle 266 connected to the system by a slide clamp 269. Phlebotomy needle 266 is also in fluid communication with a container 270 for anticoagulant. An anticoagulant pump 272 draws anticoagulant solution from container 270; the solution enters the system and mixes with drawn blood via Y-connector 268. All of the containers are typically bags made of a blood-compatible material. The depicted fluid flow path is established by suitable lengths of blood-compatible tubing (denoted collectively by reference numeral 230).

A series of air detectors D1, D2, D3, D4 detect the presence of absence of fluid at various points in the fluid circuit. A gross filter 275 (typically having a 170 $\mu$m pore size) removes potential microaggregates from blood returned to the donor. A pair of bacterial filters 277, 280 remove bacteria from solutions drawn from containers 260, 262 and 270.

In operation, controller 255 first causes tubing 230 to be primed with preservation solution from container 260 by opening valve 260v, closing valves 220v, 222v and 262v, and operating pumps 232a and 232b (although controller 255 is shown as operatively connected only to the peristaltic pumps, this is for convenience of presentation only; in fact, controller 255 governs the operation of all system elements as herein described). Pumps 232a, 232b draw preservation solution until it reaches air detector D2, which signals controller 255 as soon as the presence of liquid is sensed; controller 255 thereupon terminates the preservation-solution priming operation by closing valve 260v. During priming, valves 245v and 250v are kept open, and purged air is sent to filter 240 for accumulation in containers 245, 250.

The foregoing procedure is then repeated to prime tubing 230 with saline solution from container 262. During this operation, valve 262v is open and valves 220v, 222v and 260v are closed. Once again, priming ceases when liquid is sensed by detector D2, and purged air is sent to filter 240.

Next, controller 255 operates pump 272 to prime the tubing 230 and needle 266 with anticoagulant solution from container 270. The anticoagulant passes through tubing 230 until it reaches detector D4, which signals controller 255 as soon as the presence of anticoagulant is sensed; controller 255 thereupon terminates the anticoagulant priming operation.

With priming complete, controller 255 operates pump 232b in reverse to discharge, into bowl 210 and container 212, air in filter 240 and containers 245, 250. To accomplish this, valves 220v, 245v and 250v are open, and valves 218v, 222v, 260v and 262v are closed. Pumping continues until a pressure of 75 mm below atmospheric is detected by sensor 253.

The phlebotomy needle 266 is then inserted within the donor, and controller 255 causes whole blood to be drawn from and mixed with anticoagulant by operating pumps 232a and 272, pump 272 mixing anticoagulant from container 270 with the drawn whole blood drawn so as to maintain a target ratio (generally 1:16) of anticoagulant to whole blood. Valve 222v is open and valve 220v closed, forcing anticoagulated whole blood into bowl 210 through inlet port PT1.

Controller 255 then initiates rotation of bowl 210, and centrifugal forces separate the higher density components (mainly RBC) from lower density components (white blood cells, platelets and plasma). In particular, rotation of the centrifuge bowl concentrates RBC against the outer bowl wall. With continued ingress of blood the supernatant, comprising lighter blood components, anticoagulant and debris, forms concentric layers that approach the core of the bowl and exit out the outlet port PT2. The plasma passes through a line sensor 282 and is collected in plasma container 212, which holds approximately 400–600 ml of plasma. When nearly all separated plasma has been sent to container 212 (as indicated, for example, by increasing turbidity detected by line sensor 282, whose output is connected to controller 255), the separation process is terminated by stopping rotation of the centrifuge. Controller 255 then causes return to the donor of plasma in container 212 (again, the vertical orientation prevents infusion of any stray air) mixed with saline in a predetermined ratio by opening valves 218v and 262v and closing valve 260v; during this operation, pumps 232a, 232b rotate at identical rates, and plasma passes through the Y-connector 290 without passing to PT1. The components are preferably returned to the donor at a rapid rate, e.g., 120 ml/min. At that return rate, the saline solution is introduced by pump 232a at a rate of approximately 60 ml/min. (The addition of saline reduces the citrate effect experienced by the donor and compensates for extracted volume.) Indeed, it is possible to return plasma to the donor before completion of the cycle (i.e., even while bowl 210 is operating) by opening valves 218v and 222v, closing valve 220v and running pump 232a at a slightly faster rate than pump 232b. In this way, some of the plasma drawn from container 212 will be returned to the donor, and the remainder returned via Y-connector 290 to bowl 210 to continue the separation process. The ratio of returned to recirculated plasma is determined by the relative speeds of pumps 232a, 232b.

Blood components remaining in bowl 210 are emptied, via port PT1, through filter 240 by pump 232b with valve 222v closed and valve 220v open. Initially, in order to prime filter 240, valves 245v and 250v are kept closed, and pump 232a is operated to mix preservation solution with the contents of bowl 210; valve 260v is open and valve 262v closed. The respective rotation rates of pumps 232a, 232b are selected such that preservation solution is mixed in at a desired concentration (usually ⅓, so pump 232a rotates at ⅓ the rate of pump 232b). During this operation, which is preferably performed at a constant flow rate, air is purged from filter 240 through hydrophobic vent 225. When the pressure measured by sensor 253 reaches a predetermined limit (e.g., 150 mm Hg), the priming operation is terminated by opening one of valves 245v, 250v. The remaining contents of bowl 210 are then emptied through filter 240 until the absence of liquid is sensed by detector D2 or a predetermined volume has been processed. Preferably, during this process, controller 255 alternately opens one of valves 245v, 250v with the other valve closed in order to distribute the filtered product into containers 245, 250.

When the bowl has been emptied or the predetermined volume of product processed, apparatus 200 begins a second draw cycle identical to that described above. Whole blood is again obtained from the donor and mixed with anticoagulant, RBC accumulates in bowl 210, and plasma is returned to the donor. The second cycle is terminated (again, by signals provided by line sensor 282), and the phlebotomy needle 266 removed from the donor. This time, however, the filter priming operation is not performed; controller 255 simply operates pumps 232a, 232b at the fixed ratio of rotation rates to achieve the target mixture of preservation solution and blood product, alternately filling containers 245, 250. When bowl 210 is empty, the interior volume of filter 240 is still filled with the mixture of blood product and preservation solution. To displace this volume into containers 245, 250, controller 255 operates pump 232a to transfer additional preservation solution from container 260 into filter 240. If desired, this operation can be extended beyond what is strictly necessary for displacement, sending still further preservation solution through filter 240 in order to rinse the filter. In this case, the mixing ratio of blood product to preservation solution has been chosen to permit the introduction of this subsequent volume following displacement.

During the course of filtration, controller 255 operates pump 232b in accordance with the principles of the present invention based on the pressure detected by sensor 253. In particular, depending on the characteristics of filter 240, controller 255 can ensure a constant flow rate or a constant pressure, can trigger an alarm in response to an excessive or insufficient pressure (instantaneous or averaged over a cumulative volume), and/or can terminate flow (by disabling pump 232b and/or closing valve 220v) in response to an excessive or insufficient pressure.

Apparatus 200 can, alternatively, be configured and operated to collect multiple blood products. For example, the arrangement shown in FIG. 2 can be used to collect a plasma fraction and an RBC fraction as follows. Following collection and separation, plasma from container 212 is sent through filter 240, rather than back to phlebotomy needle 266, by closing valve 222v and keeping valve 220v open. Once again, controller 255 responds to sensor 253 and operates pump 232b in accordance with the invention, and only one of valves 245v, 250v is kept open to retain the plasma in a single collection container.

When transfer of plasma from container 212 is complete (as indicated by air detection at D2 or the measured weight of container 212), valve 218v is closed. The currently open one of valves 245v, 250v is closed and the other opened. Pumps 232a, 232b are then operated to draw RBC from bowl 210 and container 260 in a fixed ratio and force these through filter 240 (again, in accordance with the invention) and into the unfilled one of containers 245, 250. Because controller 255 is programmable, its operation can take account of differences in filter handling requirements for the different blood products; for example, the maximum filter pressure for plasma may be different from the maximum pressure for RBC. It may also be desirable, before drawing material from bowl 210, to rinse filter 240 with a small amount of saline or preservative drawn from one of containers 260, 262.

Once again, various changes to the foregoing design are possible. For example, by connecting the line leading from container 212 through valve 218v to the line leading to PT1, rather than to the line leading to pump 232a, the need to use both pumps 232a, 232b (rotating at identical rates) to return plasma to the donor is eliminated. Instead, pump 232b alone handles plasma return. A benefit of this design alteration is the ability to locate bacterial filter 280 downstream of pump 232a (e.g., between pump 232a and Y-connector 290), so that the filter does not interfere with the efficiency of pump 232a.

It is also possible to eliminate vent 225 through the addition, past filter 240 and in parallel with containers 245, 250, of a pouch that is ordinarily sealed off (e.g., by means of a tubing slide clamp) from the system, but is used to collect accumulated air from containers 245, 250 following completion the procedure. This may be accomplished by hanging containers 245, 250 in a vertical orientation and manually forcing air into the pouch. Although this design requires manual intervention, unlike the above-described configuration, it allows purging of air that would otherwise lie beyond vent 225 and thereby remain inaccessible to purging.

It will therefore be seen that the foregoing represents a convenient, safe and effective approach to blood apheresis. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. Apparatus for processing at least two blood components, the apparatus comprising:
   a. a source of at least two blood components;
   b. collection means comprising first and second separate containers for collecting first and second blood components;
   c. a controllable pump for drawing the at least one blood component from the source to the collection means;
   d. a filter for filtering at least one blood component prior to collection;
   e. means for measuring pressure into the filter;
   f. feedback means for controlling the pump based on the measured pressure and the blood component being directed through the filter;
   g. means for separately directing the first blood component through the filter and into the first container; and
   h. means for separately directing the second blood component through the filter and into the second container.

2. The apparatus of claim 1 further comprising means for withdrawing whole blood from a donor, said means comprising a phlebotomy needle.

3. The apparatus of claim 2 wherein the source of at least two blood components comprises means for separating the withdrawn whole blood into a plurality of components.

4. The apparatus of claim 3 wherein at least one separated component follows a flow path from the separating means through the filter and into the collection means, the feedback means controlling the pump so as to retain a programmed flow rate through the filter.

5. The apparatus of claim 1 further comprising alarm means actuated by the feedback means if the measured pressure exceeds a maximum limit.

6. The apparatus of claim 5 wherein the feedback means stops the pump if the measured pressure exceeds the maximum limit.

7. The apparatus of claim 1 further comprising alarm means actuated by the feedback means if the measured pressure, averaged over a predetermined flow volume, falls outside a predetermined range.

8. The apparatus of claim 3 wherein at least one separated component follows a flow path from the separating means through the filter and into the collection means, the feedback means controlling the pump so as to retain a programmed pressure into the filter.

9. The apparatus of claim 1 wherein the first blood component is plasma and the second blood component is red blood cells.

10. Apparatus for processing at least two blood components, the apparatus comprising:
    a. a source of at least two blood components;
    b. collection means for collecting the at least one blood component;
    c. means for separating the blood components;
    d. a controllable pump for directing the blood components to the collection means;
    e. a filter for filtering at least one blood component prior to collection, the filter having an internal volume, at least one separated component following a flow path from the separating means through the filter and into the collection means;
    f. means for measuring pressure into the filter;
    g. feedback means for controlling the pump based on the measured pressure;
    h. means for containing a liquid; and
    i. means for selectably coupling to the flow path and flowing the liquid therethrough to substantially displace the at least one blood component from the internal volume of the filter.

11. The apparatus of claim 1 wherein the filter is a leukocyte filter.

12. The apparatus of claim 1 wherein the filter is a bacterial filter.

13. The apparatus of claim 1 wherein the filter is a platelet-removal filter.

14. The apparatus of claim 1 wherein the filter is a viral filter.

15. The apparatus of claim 4 wherein the filter is located downstream of the pump.

16. The apparatus of claim 4 wherein the filter is located upstream of the pump.

17. A method of processing at least two blood components, the method comprising the steps of:
    a. providing a source of the at least two blood components and a filter;
    b. flowing at least one blood component from the source to the filter;

c. filtering each of the at least two blood components separately and, during said filtration, measuring pressure into the filter;

d. controlling the flow based on the measured pressure and the blood component being filtered; and e. separately collecting each of the at least two blood components.

18. The method of claim 17 further comprising the step of withdrawing whole blood from a donor to provide the at least two blood components.

19. The method of claim 18 wherein the step of providing a source of at least one blood component comprises the step of separating the withdrawn whole blood into a plurality of components.

20. The method of claim 17 wherein the withdrawal is controlled to retain a programmed flow rate through the filter.

21. The method of claim 18 further comprising the step of actuating an alarm if the measured pressure exceeds a maximum limit.

22. The method of claim 21 further comprising the step of terminating withdrawal if the measured pressure exceeds the maximum limit.

23. The method of claim 17 further comprising the step of actuating an alarm if the measured pressure, averaged over a predetermined flow volume, falls outside a predetermined range.

24. The method of claim 17 wherein the withdrawal is controlled to retain a programmed pressure through the filter.

25. The method of claim 17 wherein the first blood component is plasma and the second blood component is red blood cells.

26. A method of processing at least one blood component, the method comprising the steps of:

a. providing a source of the at least one blood component and a filter therefor, the filter having an internal volume;

b. flowing the at least one blood component from the source to the filter;

c. filtering at least one blood component and, during said filtration, measuring pressure into the filter;

d. controlling the flow based on the measured pressure; and e. pumping a liquid through the filter to substantially displace the at least one blood component from the internal volume of the filter.

27. The method of claim 17 wherein the filter is a leukocyte filter.

28. The method of claim 17 wherein the filter is a bacterial filter.

29. The method of claim 17 wherein the filter is a platelet-removal filter.

30. The method of claim 17 wherein the filter is a viral filter.

31. The method of claim 17 wherein the at least one blood component is whole blood.

* * * * *